US006614037B2

(12) United States Patent
Naito

(10) Patent No.: US 6,614,037 B2
(45) Date of Patent: Sep. 2, 2003

(54) ELECTRON BEAM IRRADIATING APPARATUS

(75) Inventor: Yoshihiko Naito, Fujisawa (JP)

(73) Assignee: Ebara Corporation, Tokyo (JP)

( * ) Notice: Subject to any disclaimer, the term of this patent is extended or adjusted under 35 U.S.C. 154(b) by 172 days.

(21) Appl. No.: 09/776,764

(22) Filed: Feb. 6, 2001

(65) Prior Publication Data

US 2001/0011710 A1 Aug. 9, 2001

(30) Foreign Application Priority Data

Feb. 7, 2000 (JP) ....................................... 2000-029330

(51) Int. Cl.[7] ............................ G21G 4/00; G21G 5/00; A61N 5/00; G21K 1/00; G21K 5/10; H01J 37/08; H01J 1/52; H01J 3/00; H01J 5/18; G21F 5/02

(52) U.S. Cl. .............................. 250/492.3; 250/423 R; 250/492.1; 250/492.24; 250/493.1; 250/503.1; 250/505.1; 250/515.1; 250/496.1; 250/498.1; 250/455.11; 313/359.1; 313/360.1; 313/363.1; 313/420

(58) Field of Search ........................... 250/492.1, 492.3, 250/423 R, 503.1, 493.1, 455.11, 496.1, 498.1, 505.1, 515.1, 492.24; 313/359.1, 360.1, 363.1, 420

(56) References Cited

U.S. PATENT DOCUMENTS

| | | | | |
|---|---|---|---|---|
| 4,331,937 A | * | 5/1982 | Brown et al. | 372/74 |
| 4,409,511 A | * | 10/1983 | Loda et al. | 313/34 |
| 4,591,756 A | * | 5/1986 | Avnery | 313/420 |
| 4,595,569 A | * | 6/1986 | Reuter et al. | 422/186 |
| 4,902,897 A | * | 2/1990 | Iwamatsu | 250/423 R |
| 5,051,600 A | * | 9/1991 | Schuetz et al. | 250/492.3 |
| 5,077,774 A | * | 12/1991 | Piestrup et al. | 378/119 |
| 5,210,426 A | * | 5/1993 | Itoh et al. | 250/492.3 |
| 5,343,047 A | * | 8/1994 | Ono et al. | 250/492.21 |
| 5,378,898 A | * | 1/1995 | Schonberg et al. | 250/492.3 |
| 5,523,577 A | * | 6/1996 | Schonberg et al. | 250/492.3 |
| 5,530,255 A | * | 6/1996 | Lyons et al. | 250/492.3 |
| 6,273,179 B1 | * | 8/2001 | Geltser et al. | 164/508 |
| 6,329,769 B1 | * | 12/2001 | Naito | 315/370 |
| 6,486,482 B1 | * | 11/2002 | Anderberg et al. | 250/492.3 |

* cited by examiner

*Primary Examiner*—John R. Lee
*Assistant Examiner*—Mary El-Shammaa
(74) *Attorney, Agent, or Firm*—Wenderoth, Lind & Ponack, L.L.P.

(57) ABSTRACT

Disclosed is an electron beam irradiating apparatus including an electron beam source; an accelerating unit for accelerating electrons emitted from the electron beam source; a deflecting unit for deflecting a highly energized electron beam generated by the accelerating unit in a scanning direction; a vacuum vessel accommodating the electron beam source, the accelerating unit, and the deflecting unit in a vacuum environment; a window foil for ejecting the electron beam from the vacuum environment into a gas environment; a crosspiece for adhering to and supporting the window foil; and a cooling block for shielding the crosspiece from the electron beam in areas that the electron beam intersects the crosspiece.

20 Claims, 4 Drawing Sheets

ELECTRON BEAM IRRADIATING APPARATUS

BACKGROUND OF THE INVENTION

1. Field of the Invention

The present invention relates to an electron beam irradiating apparatus for processing, for example, waste gas discharged from a thermal power plant. The present invention especially relates to a window foil for ejecting electrons from a vacuum vessel into a gas environment, and particularly to a crosspiece fixed to the vacuum vessel for supporting the window foil against atmospheric pressure.

2. Description of the Related Art

Some of today global problems, such as global warming and acid rain, are thought to be caused by air pollution and specifically by SOx, NOx, and other toxic components in waste combustion gases that are discharged from thermal power plants and the like. One method for removing such toxic components, as SOx and NOx, has been to conduct desulfurization and denitration by irradiating waste combustion gases with an electron beam.

FIG. 1 shows an example of an electron beam irradiating apparatus for use in such applications. An apparatus for processing waste combustion gas includes a power source 10 for generating a high DC voltage, an electron beam irradiating apparatus 11 for irradiating an electron beam onto waste combustion gas, a window foil 15 serving as an irradiating outlet for the electron beam of the electron beam irradiating apparatus 11, and a channel 19 disposed along the window foil 15 through which the waste combustion gas flows. The window foil 15 is composed of a thin plate formed of titanium or the like.

The electron beam ejected externally via the window foil 15 irradiates such molecules in the waste combustion gas as oxygen ($O_2$) and water vapor ($H_2O$) to form radicals that are extremely strong oxidizers, including OH, O, and $HO_2$. These radicals oxidize the toxic components SOx and NOx to generate intermediate products of sulfuric acid and nitric acid. The intermediate products react with ammonium gas ($NH_3$) that has already been introduced to form ammonium sulfate and ammonium nitrate, which can be recovered for use as a fertilizer. Accordingly, this type of waste gas processing system can remove such toxic components as SOx and NOx from waste combustion gas and can recover useful by-products of ammonium sulfate and ammonium nitrate for use as a fertilizer.

In this example, the electron beam irradiating apparatus 11 includes as main components a thermoelectron generator 12 such as a thermionic filament; an accelerating tube 13 for accelerating electrons emitted from the thermoelectron generator 12; a focusing electromagnet 16 for controlling a diameter of an electron beam by applying a magnetic field to a highly energized electron beam formed by the accelerating tube 13; and a scanning electromagnet 17 for deflecting the electron beam by applying a magnetic field to the electron beam after it has been focused to a specific diameter. These components are accommodated in vacuum vessels 18*a* and 18*b*, which maintain a high vacuum atmosphere of approximately $10^{-6}$ Pa. By applying a magnetic field using the scanning electromagnet 17, the highly energized electron beam is deflected in a scanning motion through the window foil 15 and ejected onto the waste combustion gas within a prescribed range of the channel 19.

As described above, this type of electron beam irradiating apparatus must eject an electron beam into the atmosphere after electrons have been accelerated in a vacuum environment. The window foil used in this electron beam irradiating apparatus is generally a film formed of pure titanium or a titanium alloy having a thickness of several tens of micrometers (for example, 40 $\mu$m) in order to attain a high electron transmission efficiency for ejecting the electron beam. The window foil 15 is mounted on an end of the vacuum vessel 18*a* via a mounting flange (not shown). The size of the window foil 15 is as large as 3 m×0.6 m. Here, an atmospheric pressure of approximately 1000 hPa is applied to a surface of the window foil, against an internal pressure of approximately $10^{-6}$ Pa in the vacuum vessel. Accordingly, a large force is applied to the window foil via a relationship of area and pressure differential. Therefore, a crosspiece is affixed to a portion of the window foil surface, thereby dividing the window foil into a plurality of sections.

FIG. 2 shows an example of a construction for dividing the window foil 15 with a crosspiece, and a scanning path for an electron beam. As described above, the window foil 15 is relatively large, i.e. 3 m by 0.6 m. A central crosspiece 21 is disposed lengthwisely across a center of the window foil 15 and adhered thereon for supporting the same. Accordingly, the crosspiece 21 supports a central portion of the window foil 15 and divides the surface of the window foil 15 into two sections. This configuration prevents the window foil 15 from deforming, even while incurring a large pressure from an atmospheric side toward an evacuated side of the window foil.

Since the electron beam is emitted over a large range through the window foil 15, which has a relatively large area, it is possible to avoid heat damage to the window foil 15. Therefore, the electron beam scans the window foil 15 in lengthwise direction thereof along a path P in the direction shown by the arrow in FIG. 2 in order to avoid heat damage to the window foil 15. At this time, the electron 20 beam scans along a path that does not traverse the crosspiece in the lengthwise direction. The electron beam is accelerated by a voltage of approximately 800 kV. Even with a large electric current of approximately 500 mA, energy loss occurs when the electron beam passes through the window foil, thereby generating a large amount of heat therein. For this reason, a cooling pipe is provided in the crosspiece 21 and cooling water is flowed through the pipe to prevent damage to the window foil 15 due to excess heat.

However, in order to scan the window foil 15 along the path P shown in FIG. 2, the electron beam inevitably must cross end portions 21*a* and 21*b*. When the electron beam E crosses these portions and irradiates the end portions 21*a* and 21*b*, a large amount of heat is generated on these portions of the crosspiece 21. Over extended use, this excess heat can cause thermal fatigue in portions of the cooling water pipe provided in the crosspiece 21, leading to such accidents as water leaking into the evacuated section. If the vacuum vessel becomes contaminated, it is necessary to disassemble the electron beam irradiating apparatus to repair the damage and then reassemble the apparatus. This process requires much time and labor. Further, once the damage has been repaired, more time is required to evacuate the vacuum vessel again, thereby requiring that operations be suspended for a considerably long time, in addition to difficult repair work.

SUMMARY OF THE INVENTION

In view of the foregoing, it is an object of the present invention to provide an electron beam irradiating apparatus for scanning an electron beam across an entire surface of a window foil, wherein the window foil is reinforced by a crosspiece capable of preventing excess heat from being generated due to electron beam irradiation, thereby enabling the apparatus to perform stable operations for an extended time. It is another object of the present invention to provide such an electron beam irradiating apparatus that is easy to maintain.

These objects and others will be attained by an electron beam irradiating apparatus comprising an electron beam source for emitting electrons; an accelerating unit for accelerating electrons emitted from the electron beam source to generate a highly energized electron beam; a deflecting unit for deflecting the highly energized electron beam generated by the accelerating unit in a scanning direction; a vacuum vessel accommodating the electron beam source, the accelerating unit, and the deflecting unit in a vacuum environment; a window foil for ejecting the electron beam from the vacuum environment into a gas environment; a crosspiece for adhering to and supporting the window foil; and a cooling block for shielding the crosspiece from the electron beam in areas that the electron beam intersects the crosspiece.

With this construction, the cooling block can prevent excess heat from being generated in portions of the crosspiece over which the electron beam passes by receiving irradiation of the electron beam at these portions. This construction allows stable operation of the electron beam irradiating apparatus.

According to another aspect of the present invention, the cooling block can be detachably mounted. With this construction, the cooling block can be easily replaced after incurring fatigue by irradiation of an electron beam over a long period of time. Therefore, the present invention can prevent such serious accidents as water leakage and the like through regular replacement of the cooling block.

According to another aspect of the present invention, the cooling block includes a cooling pipe formed of a metal material and has a fluid therein. With this construction, the cooling block can be easily manufactured, and a portion of the cooling block irradiated by an electron beam can be easily cooled.

According to another aspect of the present invention, a cross-section of the cooling block is gently curved on a side facing the electron beam source. With this construction, an electron beam evenly irradiates a surface of the cooling block, thereby preventing excess heat from energy of the electron beam from being concentrated on a portion of the block.

DETAILED DESCRIPTION OF THE PREFERRED EMBODIMENTS

An electron beam irradiating apparatus according to preferred embodiments of the present invention will be described with reference to FIGS. 3 and 4.

Figure 3:
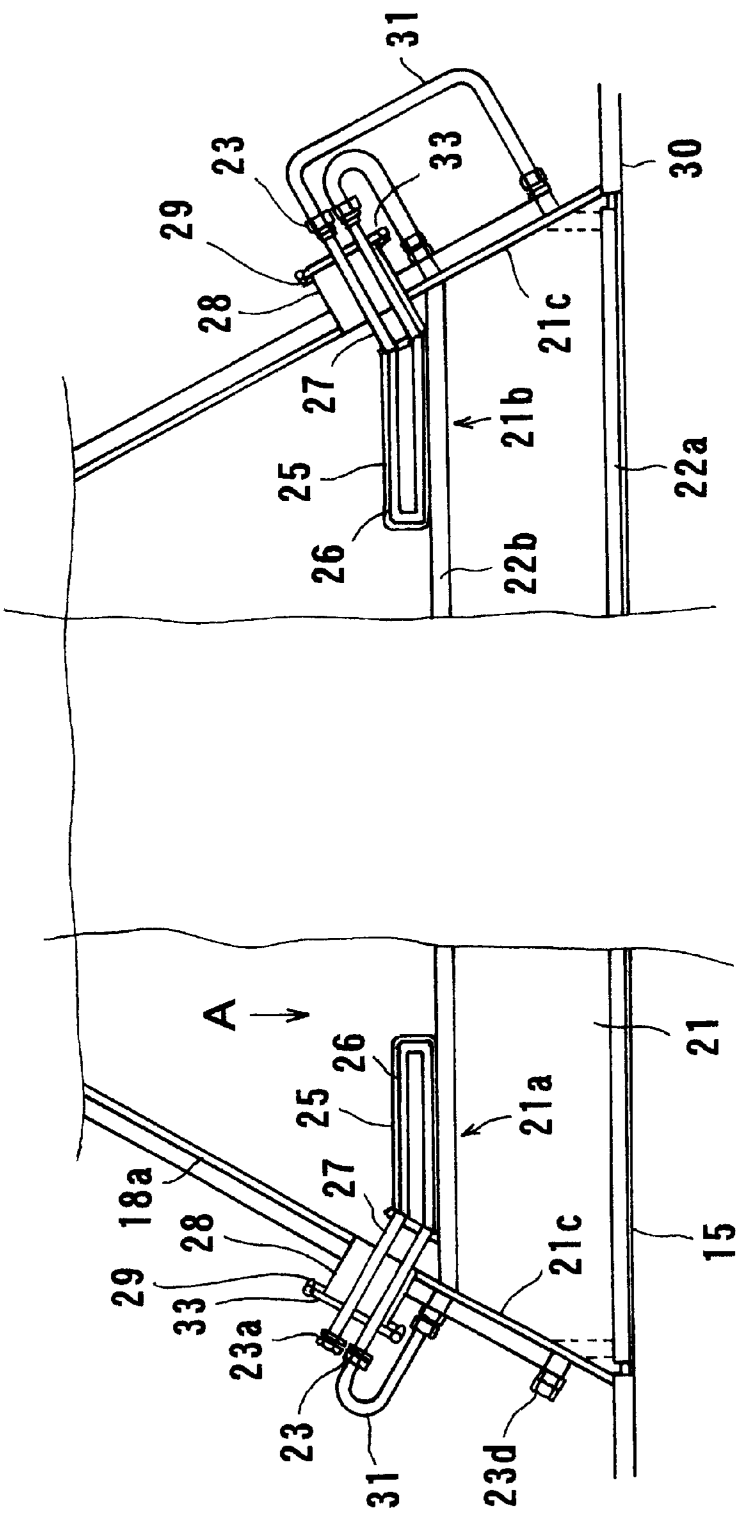
FIG. 3 is a cross-sectional view showing a construction of a cooling block in an electron beam irradiating apparatus of a first embodiment.

FIG. 3 is a cross-sectional view showing a construction of a window foil and a surrounding area in an electron beam irradiating apparatus. FIG. 4 shows a detailed construction of a cooling block. Parts similar to those described above are referred to using the same part number.

Figure 1:
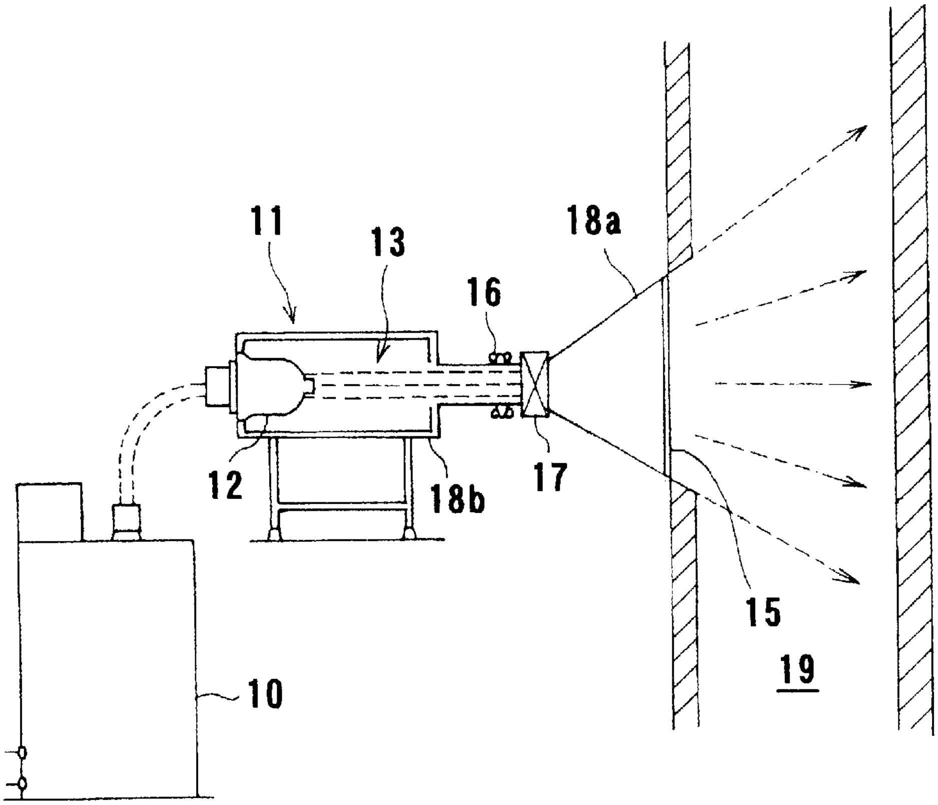
FIG. 1 is an explanatory diagram showing an overall construction of an electron beam irradiating apparatus.
Figure 2:
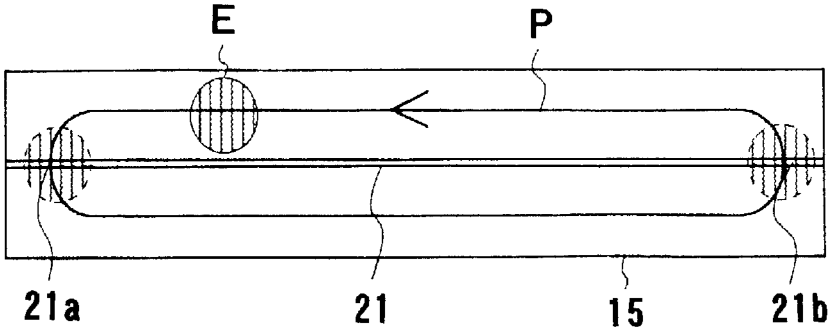
FIG. 2 is an explanatory diagram showing a position of a crosspiece in the electron beam irradiating apparatus of FIG. 1 and a scanning path of an electron beam.

Window foil 15 formed of titanium material is fixed to a bottom surface of vacuum vessel 18*a* via a flange 30. Crosspiece 21 is disposed at a central bottom portion of the vacuum vessel 18*a*. A bottom surface of the crosspiece 21 is affixed to the window foil 15 to prevent the window foil 15 from deforming due to atmospheric pressure when the vacuum vessel 18*a* is maintained in a high vacuum state. The crosspiece 21 is formed of a stainless steel material having a width of approximately 3 centimeters and a height of approximately 40 centimeters. The crosspiece 21 is disposed across a central portion of the window foil 15. The window foil 15 has a surface area of 3×0.6 meters, as shown in FIG. 2. Both lengthwise ends of the crosspiece 21 are joined to the vacuum vessel 18*a* by portions 21*c*. With this construction the window foil 15 is reinforced against strong pressure applied from an atmospheric side of the window foil. Cooling pipes 22*a* and 22*b* are provided inside the crosspiece 21. Cooling water flowed through the cooling pipes 22*a* and 22*b* absorb heat generated by electron beams penetrating the window foil 15 because of good thermal conductivity of the window foil material, and also absorb heat generated from the electron beam directly ejected on a top surface of the crosspiece 21.

In the electron beam irradiating apparatus of the present invention, a cooling block 25 is disposed over end positions 21*a* and 21*b*, over which portions of the crosspiece 21 an electron beam crosses when scanning between lengthwise directions of the crosspiece. In other words, the cooling block 25 serves to protect the crosspiece 21 by shielding the same from irradiation by the electron beam. The cooling block 25 has a width of 36 millimeters, which is slightly larger than the width of the crosspiece 21, and a length of approximately 35 centimeters. The cooling block 25 is sufficiently large to block an entire scanning diameter of the electron beam. The cooling block 25 is formed of aluminum, copper, silver, or the like, and has a thermal conductivity of 200 $W*m^{-1}*k^{-1}$ or greater. A water channel 26 is formed inside the cooling block 25. Cooling water flowed through the water channel 26 absorbs heat generated by irradiation from the electron beam. A stainless steel pipe 27 is connected to the water channel 26. The stainless steel pipe 27 is configured to penetrate a plate member 33 for fixing the stainless steel pipe 27, and an end of the stainless steel pipe 27 protrudes outside of the vacuum vessel 18*a*. The plate member 33 is detachably fixed by a bolt or the like to a flange 29 of a bracket 28. A piping 31 connects the stainless steel pipe 27 to the cooling pipes 22*a* and 22*b*. Cooling water is supplied through a supply terminal 23*a*. The cooling water circulates through the water channel 26 on a left side of the cooling block 25, then flows into the cooling pipe 22*b* on top of the crosspiece 21. From here, the cooling water flows through the cooling block 25 on the right side of the cooling block and then returns to the cooling pipe 22*a* on the bottom of the crosspiece 21. The cooling water is discharged from a discharge terminal 23*d*.

Figure 4A:
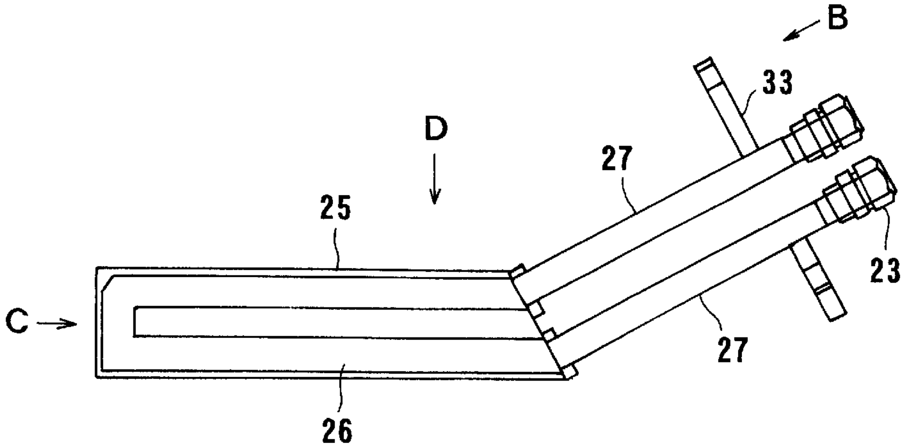
FIGS. 4A–4D include a front view (FIG. 4A), a view (FIG. 4B) indicated by arrow B in FIG. 4A, a view (FIG. 4C) indicated by arrow C in FIG. 4A, and a view (FIG. 4D) indicated by arrow D in FIG. 4A, showing a detailed construction of the cooling block of FIG. 3.
Figure 4B:
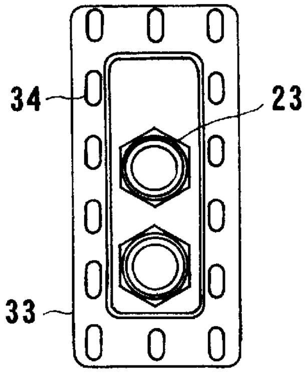
Figure 4C:
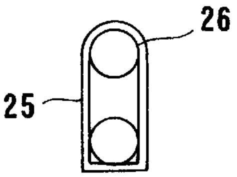
Figure 4D:
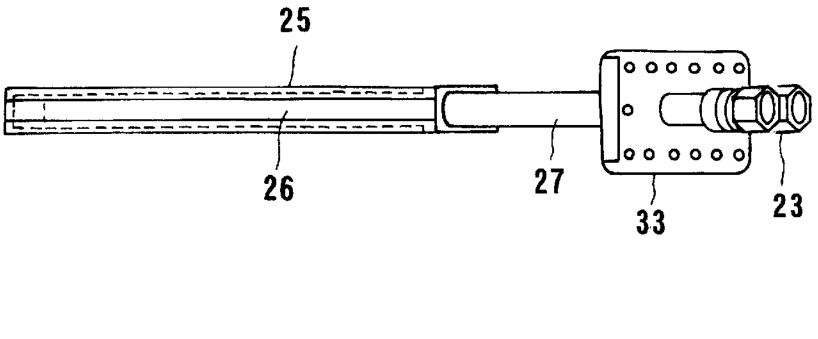

FIGS. 4A–4D show a more detailed construction of the cooling block 25. As shown in FIG. 4A, the water channel 26 is formed in the cooling block 25, which in this case is copper. As shown in FIG. 4C, a cross-section of the cooling block 25 is substantially rectangular in shape. A top end of the cooling block 25 curves gently as a semicircle. The stainless steel pipe 27 is fixed to both open ends of the water channel 26 by silver brazing. The stainless steel pipe 27 is welded to the plate member 33 at a portion thereof through which the stainless steel pipe 27 penetrates. A terminal is fixed to an external end of the stainless steel pipe 27 for connecting the stainless steel pipe 27 to piping for supplying cooling water. FIG. 4B shows a view indicated by arrow B in FIG. 4A. As shown, a plurality of generally rectangular bolt holes 34 are formed in the plate member 33 for detachably bolting the plate member 33 to the flange 29. FIG. 4D shows a view indicated by arrow D in FIG. 4A. As shown, the stainless steel pipe 27 is connected to the cooling block 25 at an angle. Another end of the stainless steel pipe 27 is fixed to the plate member 33.

Next, a function of the cooling block will be described. As described above, the cooling block 25 is integrally fixed to the stainless steel pipe 27 and plate member 33. By fixing this assembly to through-holes in the bracket 28 of the vacuum vessel 18*a*, the cooling block 25 can shield and protect the crosspiece 21 from the electron beam, as the electron beam passes over the end portions 21*a* and 21*b*. The plate member 33 is fixed by bolts or the like to the flange 29 to form a vacuum seal. Next, piping for introducing cooling water is connected to terminals of the pipes shown in FIG. 3. During operations of the electron beam irradiating apparatus after the vacuum vessel 18*a* has been evacuated, the electron beam scans a path shown in FIG. 2, crossing the end portions 21*a* and 21*b* of the crosspiece 21. Although the electron beam irradiates the cooling block 25 at these portions, the cooling block 25 shields and protects the crosspiece 21 so that temperature of the crosspiece 21 does not rise at all. Accordingly, the cooling block 25 prevents occurrence of leakage or other accidents caused by fatigue of the crosspiece 21. Heat is generated in the window foil 15 due to transmission of the electron beam. However, as described with regard to conventional apparatus, cooling water in the crosspiece 21 cools the window foil 15.

The cooling block 25, on the other hand, can rise in temperature when incurring direct contact from the electron beam. However, with cooling water circulating through the water channel 26 formed in the cooling block 25, such temperature rise can be prevented. Still, it is a fact that fatigue or the like can occur in the cooling block 25 due to great energy loss caused by irradiation of the electron beam. For this reason, the cooling block 25 is configured to be detachable and should be replaced on a regular basis. If the cooling block 25 is replaced regularly, it is possible to prevent serious accidents, such as leakage. Although, water is ordinarily used as a cooling medium in the cooling block 25, a substitute for water can also be selected according to the irradiating apparatus. Examples of substitutes include alcohol or other liquids and cooling gases such as He, $N_2$, and Ar.

Figure 5:
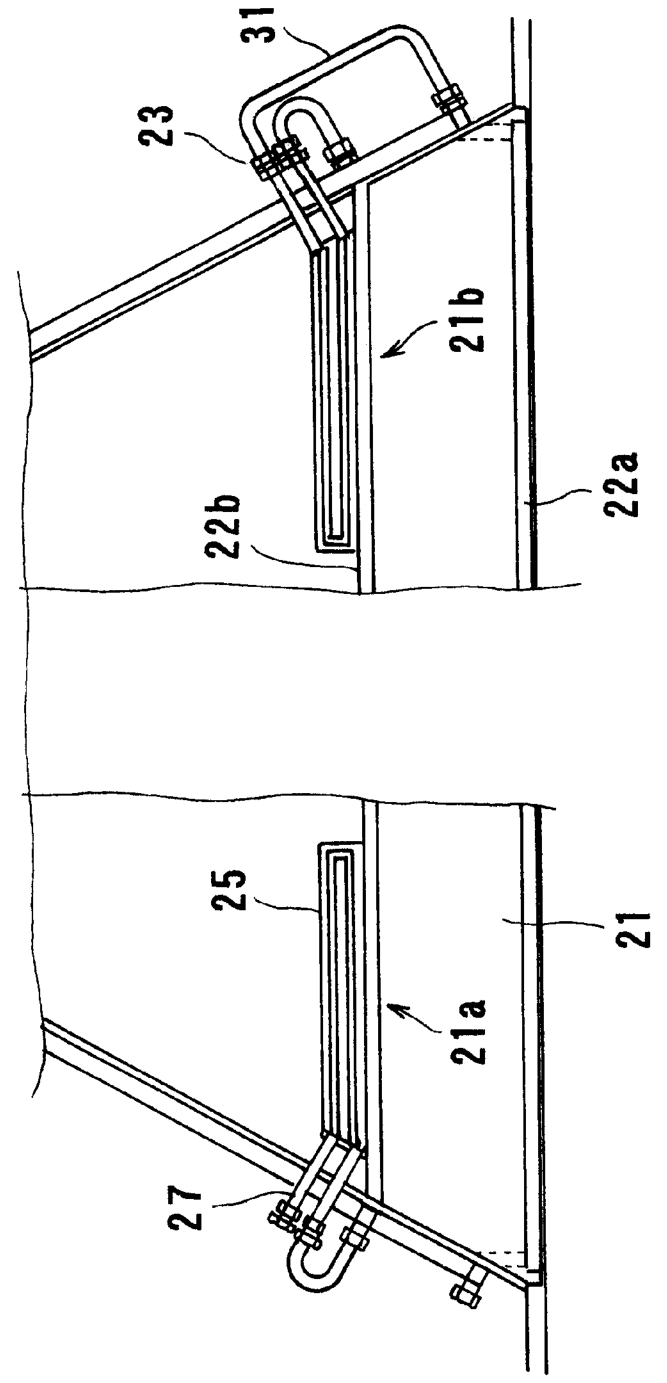
FIG. 5 is a cross-sectional view showing a construction of a cooling block in an electron beam irradiating apparatus of a second embodiment.

FIG. 5 shows an electron beam irradiating apparatus according to a second embodiment of the present invention. The construction of cooling block 25 is similar to that in the first embodiment. Stainless steel pipe 27 is connected to a water channel formed in the cooling block 25. A connecting terminal 23 is provided at an end of the stainless steel pipe 27 for connecting the stainless steel pipe 27 to external piping 31. A construction for flowing cooling water is the same as that described in the first embodiment. Further, a function of the cooling block 25 for shielding crosspiece 21 from the electron beam as the beam passes over end portions 21*a* and 21*b* is also the same as that described in the first embodiment. Accordingly, by shielding and protecting the crosspiece 21 from irradiation by the electron beam, the cooling block 25 prevents leakage or other accidents as described above. However, the stainless steel pipe 27 is fixed via a fixing member to vacuum vessel 18*a* using a brazing process or the like. As a result, the cooling block 25 cannot be easily detached. However, by converting existing electron beam irradiating apparatus to this construction, the cooling block 25 can shield and protect the crosspiece 21 from electron beam irradiation. Further, repair of the cooling block 25 is relatively easy in the event that metal fatigue occurs therein.

In the embodiments described above, the present invention employs a cooling block to shield portions of a crosspiece overwhich an electron beam crosses to prevent overheating of and damage to the crosspiece. As a result, the electron beam irradiating apparatus can be operated stably for an extended time, thereby improving reliability of the electron beam irradiating apparatus. Also, by making the cooling block detachable, it is possible to regularly replace the cooling block, thereby facilitating maintenance and preventing accidents due to damage to the cooling block itself.

While a cooling block for protecting a center crosspiece in an electron beam irradiating apparatus having an oblong window foil has been described in detail with reference to specific embodiments thereof, it will be apparent to those skilled in the art that many modifications and variations may be made therein without departing from the spirit of the invention, the scope of which is defined by the attached claims.

What is claimed is:

1. An electron beam irradiating apparatus comprising:

an electron source for emitting electrons;

an accelerating unit for accelerating electrons emitted from said electron source to generate an electron beam;

a deflecting unit for deflecting in a scanning direction the electron beam generated by said accelerating unit;

a vacuum vessel accommodating said electron source, said accelerating unit, and said deflecting unit in a vacuum environment;

a window foil for ejecting the electron beam from the vacuum environment into a gas environment;

a crosspiece for adhering to and supporting said window foil, said crosspiece being disposed lengthwise across a center of said window foil so as to divide a surface of said window foil into two sections, wherein said deflecting unit is for deflecting the electron beam so as to intersect said crosspiece; and a cooling block for shielding said crosspiece from the electron beam, when deflected by said deflecting unit, at areas that the electron beam intersects said crosspiece.

2. The electron beam irradiating apparatus as recited in claim 1, wherein said cooling block is detachably mounted.

3. The electron beam irradiating apparatus as recited in claim 1, wherein said cooling block includes a first cooling pipe formed of a metal material through which a fluid is to flow.

4. The electron beam irradiating apparatus as recited in claim 1, wherein a cross-section of said cooling block is gently curved on a side facing said electron beam source.

5. The electron beam irradiating apparatus as recited in claim 1, wherein said cooling block is disposed on said crosspiece at the areas of said crosspiece intersected by the electron beam when deflected by said deflecting unit and upon the electron beam scanning along lengthwise directions of said crosspiece.

6. The electron beam irradiating apparatus as recited in claim 3, further comprising a second cooling pipe in said crosspiece, wherein said first cooling pipe is in said cooling block and is connected to said second cooling pipe.

7. The electron beam irradiating apparatus as recited in claim 5, wherein said cooling block has a width that is slightly larger than a width of said crosspiece.

8. The electron beam irradiating apparatus as recited in claim 1, wherein said cooling block is substantially formed of thermal conductive material having a thermal conductivity of at least 200 $W \cdot m^{-1} \cdot K^{-1}$.

9. An electron beam irradiating apparatus comprising:

an electron source for emitting electrons;

an accelerating unit for accelerating electrons emitted from said electron source to generate an electron beam;

a deflecting unit for deflecting in a scanning direction the electron beam generated by said accelerating unit;

a vacuum vessel accommodating said electron source, said accelerating unit, and said deflecting unit in a vacuum environment;

a window foil for ejecting the electron beam from the vacuum environment into a gas environment; and a crosspiece for adhering to and supporting said window foil, said crosspiece being disposed lengthwisely across a center of said window foil so as to divide a surface of said window foil into two sections, wherein said deflecting unit is for deflecting the electron beam so as to intersect said crosspiece; and a cooling block for shielding an area from the electron beam when deflected by said deflecting unit, said cooling block being disposed where the electron beam is irradiated on said window foil when deflected by said deflecting unit.

10. The electron beam irradiating apparatus as recited in claim 5, wherein the areas to be intersected by the electron beam correspond to end portions of said crosspiece.

11. The electron beam irradiating apparatus as recited in claim 3, wherein said crosspiece includes a second cooling pipe which is connected to said first cooling pipe.

12. The electron beam irradiating apparatus as recited in claim 9, wherein said cooling block is detachably mounted.

13. The electron beam irradiating apparatus as recited in claim 9, wherein said cooling block includes a first cooling pipe formed of a metal material through which a fluid is to flow.

14. The electron beam irradiating apparatus as recited in claim 13, further comprising a second cooling pipe in said crosspiece, wherein said first cooling pipe is in said cooling block and is connected to said second cooling pipe.

15. The electron beam irradiating apparatus as recited in claim 13, wherein said crosspiece includes a second cooling pipe which is connected to said first cooling pipe.

16. The electron beam irradiating apparatus as recited in claim 9, wherein a cross-section of said cooling block is gently curved on a side facing said electron beam source.

17. The electron beam irradiating apparatus as recited in claim 9, wherein said cooling block is disposed on said crosspiece at areas of said crosspiece intersected by the electron beam when deflected by said deflecting unit and upon the electron beam scanning along lengthwise directions of said crosspiece.

18. The electron beam irradiating apparatus as recited in claim 17, wherein the areas to be intersected by the electron beam correspond to end portions of said crosspiece.

19. The electron beam irradiating apparatus as recited in claim 17, wherein said cooling block has a width that is slightly larger than a width of said crosspiece.

20. The electron beam irradiating apparatus as recited in claim 9, wherein said cooling block is substantially formed of thermal conductive material having a thermal conductivity of at least 200 $W \cdot m^{-1} \cdot K^{-1}$.

* * * * *